US006899897B2

(12) United States Patent
Battaglia

(10) Patent No.: US 6,899,897 B2
(45) Date of Patent: May 31, 2005

(54) GUM RESIN AS A CARRIER FOR TOPICAL APPLICATION OF PHARMACOLOGICALLY ACTIVE AGENTS

(75) Inventor: Alex Battaglia, La Jolla, CA (US)

(73) Assignee: Jaleva, Inc., La Jolla, CA (US)

( * ) Notice: Subject to any disclaimer, the term of this patent is extended or adjusted under 35 U.S.C. 154(b) by 0 days.

(21) Appl. No.: 10/053,313

(22) Filed: Jan. 18, 2002

(65) Prior Publication Data

US 2003/0099666 A1 May 29, 2003

Related U.S. Application Data

(60) Provisional application No. 60/299,377, filed on Jun. 18, 2001.

(51) Int. Cl.$^7$ .............................. A61K 9/14; A61K 9/70; A61K 15/16; A61K 9/16
(52) U.S. Cl. ...................... 424/485; 424/443; 424/446; 424/448; 424/449; 424/496
(58) Field of Search ................................ 424/485, 496, 424/443, 446, 448, 449

(56) References Cited

U.S. PATENT DOCUMENTS

| | | | |
|---|---|---|---|
| 4,307,075 A | 12/1981 | Martin | |
| 5,063,065 A | 11/1991 | Bazterrica et al. | 424/637 |
| 5,167,649 A | 12/1992 | Zook | 604/307 |
| 5,429,590 A | 7/1995 | Saito et al. | |
| 5,446,070 A * | 8/1995 | Mantelle | 514/772.6 |

OTHER PUBLICATIONS

U.S. Appl. No. 60/299,377, filed Jun. 18, 2001, Battaglia et al.
Goh, et al., *Singapore Med. J.* (1998) 39:17–19.
Moher and Maurer, (1979) *J. Family Practice* 9:237–240.
Simmons, (1981) *Br. J. Vener. Dis.* 57:208–209.
Bennet and Grist (1985) (1985) *Southern Medical J.* 78:224–225.
Lim et al. (1987) *Annals Academy of Medicine* 16:167–169.
Ozumba and Megafu (1991) *Int J Gynecol Obstet* 34:347–352.
Reynolds et al. (1993) *Int J of STD & AIDS* 4:226–231.
"Podocon–25" retrieved Jun. 16, 2003 from http://www.stanford.edu/group/virus/1999/thanatos/podophyillin.html.
"Tinctura Benzoini" King's American Dispensatory, by Harvey Felter & John Lloyd, 1898 retrieved Jun. 16, 2003 from http://www.ibiblio.org/herbmed/eclectic/kings/styrax–benz_tinc.html.
"Benzoinum" King's American Dispensatory, by Harvey Felter & John Lloyd, 1898 retrieved Jun. 16, 2003 from http://www.ibiblio.org/herbmed/eclectic/kings/styrax–benz.html.
"Podocon–25" Material Safety Data Sheet retrieved Jun. 19, 2003 from http://www.paddocklabs.com/forms/msds/podocon.pdf.
"Podophyllum (Topical)" from Thomson MICROMEDEX, 2003 retrieved Jun. 19, 2003 from http://health.yahoo.com/health/drugs/202469/_overview.html.
"PDR entry for Podocon–25 Liquid" from American health Consultants, Inc., 2001 retrieved Jun. 19, 2003 from http://www.ctclconsult.com/pdrdruginfo/html/61201000.htm.

* cited by examiner

Primary Examiner—Theodore J. Criares
(74) Attorney, Agent, or Firm—Gray Cray Ware & Freidenrich, LLP

(57) ABSTRACT

The invention provides a biological dressing for treatment of a dermatological disease comprised of a gum resin, a topically acceptable volatile solvent, and a pharmacologically active agent. The gum resin is present in a suitable amount that the composition, when the solvent evaporates, will dry to form a solid coating that sticks to the skin or mucosal membrane to which the composition is applied and maintain the pharmacologically active agent over a sustained period of time in contact with sites on the skin or mucosal membranes exhibiting symptoms of the disease. Methods are provided for treating symptoms of dermatological diseases with such a pharmacological composition. Biological dressings including tincture of benzoin and clotrimazole are shown to be efficacious for the long-term amelioration of symptoms of athlete's foot.

25 Claims, No Drawings

GUM RESIN AS A CARRIER FOR TOPICAL APPLICATION OF PHARMACOLOGICALLY ACTIVE AGENTS

CROSS REFERENCE TO RELATED APPLICATIONS

This application claims benefit of priority to provisional application U.S. Ser. No. 60/299,377 filed Jun. 18, 2001, which disclosure is hereby incorporated by reference.

INTRODUCTION

1. Technical Field

The invention relates to gum resin based biological dressings that adhere to the skin and contain one or more pharmacologically active agents for the treatment of symptoms relating to dermatological diseases and those affecting mucous membranes. The invention is exemplified by biological dressings comprising tincture of benzoin and clotrimazole for the treatment of athlete's foot.

2. Background

For many forms of dermatological conditions, the powders, sprays, solutions, lotions and creams available over-the-counter lack effectiveness. The reason for this varies, from poor delivery of the medication to the source or cause of the condition, to loss of the medication through abrasion from normal activity of the patient, to absorption of medications applied to the skin by the patient's socks or clothes. For these various reasons, currently available commercial medications are prone to come off easily once applied to the affected area, and consequently much of the medication is wasted, either through over application in an attempt to anticipate the problem, or in medicine quickly being dispersed away from the site. The medications for these conditions typically require at least 2 to 4 weeks of continuous treatment, and thus often fail due to this poor delivery.

A further problem with the use of existent medications is the lack of compliance by patients. Due to the mess and difficulty of use, patients will often use these over the counter medications only until their symptoms abate and then they will stop the medication, before the recommended course of treatment is completed, and hence often before the infection has truly cleared. Though momentarily abated, the infection then begins to take hold again, and in a matter of days or weeks a full blown infection occurs again. In many cases the patient will repeat using the over the counter medication until the symptoms clear, and again stop the medication with the first sign of abatement, with the whole cycle repeating.

Hence, there is a need for a clean and inexpensive vehicle/carrier of topically applied medications that increases the convenience and effectiveness of the treatment and decreases the necessary time for the treatment. It is preferably associated with less waste and lower cost and ultimately leads to improved treatment of patient symptoms and increased patient satisfaction.

3. Description of Related Art

In medicine, tincture of benzoin and mastic gum (Mastisol) have been employed to form a sticky coating on skin prior to the placement of adhesive preparations. Tincture of benzoin has also been used to form a biologic dressing over superficial cutaneous wounds as well as apthous ulcers (canker sores). However, the general use of gum resins, such as mastic gum and benzoin gum, as semi-permanently applied carriers for increasing the efficacy and usefulness of topological of pharmacological agents has not been disclosed.

A tincture of benzoin has been used with podophyllin resin (10–25%) in the treatment of genital warts. It is considered by many to be cumbersome and inconvenient (see U.S. Pat. Nos. 5,063,065 and 5,167,649). Unfortunately, podophyllin resin is toxic, and even when applied in a tincture of benzoin, this agent must be removed by rigorous washing 1 to 6 hours post-application. Due to the problems associated with using podophyllin resin in tincture of benzoin, other carriers have been sought. As an example, in the treatment of genital warts, Goh, et al. (*Singapore Med J* (1998) 39:17–19) reports that podophyllin prepared in 0.25% ethanol can be self-applied and is as efficacious as podophyllin prepared in tincture of benzoin and applied in the clinic. Use of tincture of benzoin as a biological bandage with compounds that it is desirable to have in long contact with the skin has not been reported.

SUMMARY OF THE INVENTION

Compositions and methods are provided for increasing the effectiveness of treatment of dermatological disorders on the skin or a mucous membrane of a mammal by using a gum resin as a carrier for a pharmacologically active agent. The pharmacological compositions are comprised of a gum resin, at least one topically acceptable pharmacologically active agent for treatment of a dermatological disorder other than the gum resin, wherein the active agent is non-toxic to the mammal being treated when left in contact with the lesion of interest for at least 6 hours, and a topically acceptable volatile solvent. The compositions optionally can include a penetration enhancer. The methods of treating symptoms of a dermatological disorder include the steps of contacting affected sites on the skin of a patient in need thereof with the pharmacological composition comprised of a gum resin, a pharmacological agent or agents, and an evaporative solvent, and allowing it to dry to form a biological dressing. The biological dressing comprises a sticky film of gum resin and a pharmacologically active agent left on the skin or mucous membrane after the volatile solvent has evaporated. The dressing forms a hydrophobic, protective film that provides sustained release of the pharmacologically active agent at the site of application. The invention finds use in the treatment of dermatological disorders such as infection, inflammation, and hyperproliferation of epidermal cells.

DETAILED DESCRIPTION OF THE INVENTION

Compositions and methods are provided for the convenient and effective treatment of at least one symptom of a dermatological disorders in a mammal, particularly a human, in need thereof, with a biological dressing. By "biological dressing" or "biologic dressing" or "biologic bandage" is intended a non-occlusive but adherent pharmacological composition that is formed by drying on the skin a pharmacologic composition comprised of a gum resin, such as benzoin or mastic gum, a pharmacologically active agent and topically acceptable volatile solvent, such as ethanol. The biologic dressing forms a protective coating at the site(s) on the skin or mucosal membrane exhibiting symptoms of the disorder and also acts as a reservoir for the pharmacolocally active agent(s) to provide sustained delivery of an appropriate medication or combination of medications to the site. The skin disorder symptoms to be treated include skin and mucosal membrane lesions, inflammation, itching, scaling and pain. The disorders include viral, fungal and bacterial infections, inflammatory conditions, and hyperproliferative disorders. The pharmacological agent(s) can include topically active agents that can be used to ameliorate skin disorder symptoms, including antimicrobial and antiviral agents, anti-inflammatory agents, analgesics and anesthetics. As desired, the effectiveness of the pharmacological agent(s) optionally can be increased by including skin a penetration enhancer in the pharmacologic composition. The biological bandage is easily removed using a solvent such as ethanol. Since the coating that contains the medication stays in place until such deliberate removal, the effectiveness of the treatment is increased since the skin is exposed to the active ingredient for a longer period of time. This also allows for a decreased treatment time, and, ultimately, improved treatment of symptoms and increased patient satisfaction. Thus, compositions of the invention can be used to improve delivery of medications that are soluble in organic solvents such as alcohols that are typically applied topically for the treatment dermatologic disorders.

The advantages of the subject invention include a more specifically directed application of medications to sites affected by a skin disorder, and extended retention on the skin of the medication because the film is resistant to water and abrasion by clothing. Additionally, the vehicle is relatively inexpensive, is pleasant smelling, and the bandage can be conveniently and easily removed, for example with alcohol, when desired. Many dermatological conditions are exacerbated by moisture so the water repellent qualities of the dressing also protect the skin from further damage. The biological dressings are designed to be directly applied to a lesion needing treatment, and left in place for an extended period of time, without requiring conventional adhesive bandages. It is intended that the dressing need only be washed from the lesion for purposes of convenience and cleanliness. The biological dressings of the subject invention are cleaner and easier to apply than conventional dressings and existing medications, have less waste and are more economical, allowing for more efficient, efficacious and palatable relief of symptoms or recovery from the skin disorder being treated. A further advantage of the subject invention is that various of the gum resins that find use, including benzoin and mastisol, are already approved for human use and have been tested and found to be safe for topical application on non-human mammals.

The biological dressings are prepared by drying on the skin, a pharmacological composition comprising an agent that can be used to ameliorate the symptoms of a dermatological disease and a gum residue dissolved in a volatile solvent. Generally, the pharmacological composition is prepared as a sticky slurry or solution that can be applied to a site on the skin or a mucosal membrane. The consistency of the pharmacological composition can be varied by adjusting the ratio of solvent to gum residue in the composition to achieve the desired consistency for application to a particular site. For areas where evaporation of solvent may be slower, for example, application to lesions on a mucosal membrane such as the gums, it may be desirable to prepare the composition as a paste and to use a more volatile solvent, whereas for application to hard to reach areas, such as between the toes, it may be desirable to prepare a less viscous composition that can be applied thinly to the affected areas. However, for treatment of more severe lesions in non-visable areas, due to an athlete's foot infection for example, application of a more viscous preparation may be preferred. The relative proportions of the gum resin carrier, the pharmacologically active agent or agents and the evaporative solvent in the preferred composition can vary widely, and will depend upon the specific intended use of the biological dressing. Precise preferred ratios will depend to some extent on the rate of release of the pharmacologically active agent from the film, the desired stickiness of the residual film, and the area of application. For example, if the intended application is to an affected area on the face, the preferred composition would have a lower proportion of gum resin, to allow for a more thinly applied and less visible and less sticky medical dressing. Generally, the pharmacological compositions of the subject invention will have at least about 10% gum resin, more likely about 20%, 30% or 40% gum resin, as much as 50% or 60% gum resin.

The stickiness of the biological dressings is provided by the use of a gum resin, generally, naturally occurring gum resins, such as those that are harvested from trees are used, although gum resins also may be prepared by synthetic means (see for example, U.S. Pat. Nos. 5,644,049, 5,429,590 and 4,307,717). Preferred gum resins include benzoin resinous exudate harvested from *Styracaceae* trees, including Benzoin Siam from *Styrax tonkinesis* and Benzoin Sumatra from *Styrax benzoin*. Tincture of benzoin and benzoin compound tincture is readily available through numerous commercial sources, including many drug stores and suppliers of surgical goods. Another resinous tree exudate that is preferred and is commonly used in the medical arts for enhancing the adherence of surgical bandages, is mastic gum, which is harvested from *Pistacia lentiscus*. A tincture of mastic gum (Mastisol) is produced by Ferndale Laboratories in Ferndale, Mich. and is also available through suppliers of surgical goods. Other gum resins that can be used include the gum resin exudate from *Burserceae* trees, including *Boswellia serrata* (also known as Boswellin), *Boswellia dalzielli, Boswellia carteri* (gum olibanum) and *Canarium luzonicum* or *Canarium commune* (Elemi gum or resin). Additional resinous exudates contemplated from other tree species include *Eucalyptus* species (*Eucalyptus globulus*) and *Myrtaceae* "Tea-tree" species (*Melaleuca alternifolia, Leptospermum scoparium,* and *Kunzea ericoides*). Many naturally occurring gum resins themselves have pharmacological properties, and their topical application may cause irritation in certain patients or exacerbate certain conditions. Prudent choice of gum resin to be used in preparing a particular biological dressing will take into consideration the dermatological disorder to be treated and the sensitivities of a particular patient's skin.

A desirable feature of the subject compositions is that they dry to form a sticky, adherent and protective film or biological bandage over a dermatologic lesion. To effect this attribute, the pharmacological composition is prepared with a volatile solvent that evaporates to leave a hydrophobic coating comprised of the gum resin and the pharmacological agent on the skin. Volatile solvents for use in the subject compositions include alcohols such as methanol, ethanol, propanol, and isopropanol, and ketones, such as acetone. Other evaporative compounds may also find use, so long as they are compatible with other components of the pharmacological composition and topically acceptable to the majority of patients. The gum resin of choice is diluted in the volatile solvent such that the concentration of solvent comprises at least about 40% or 50% (v/v or v/w), more commonly at least about 60%, 70% or 80%, or as much as about 90% of the total composition. A particularly preferred composition is a tincture of benzoin, which is comprised of benzoin in about 60%, 70%, 80% or 90% ethanol.

The pharmacological agent or agents included in the pharmacological compositions will depend upon the dermatological disorder being treated. To allow for extended contact of the biological dressing with the lesion under treatment, pharmacological agents chosen should be efficacious without being locally or systemically toxic or caustic to the mammal to which the medicated dressing is administered. A biological dressing of the subject invention is intended to remain at the site of application for at least 6 hours, more often as long as 8, 10 or 12 hours, sometimes as long as 16, 18 or 20 hours, and for certain treatments, as long as 24, 36 or 72 hours or even longer prior to removal. The time of treatment desired is based at least in part upon the nature of the condition to be treated and the pharmacological agent(s) that are being used. In general, the pharmacological compositions are formulated so that the concentration of the pharmacological agent(s) that is in the biological bandage approximates the concentration of agent that is used in existing topical formulations. However, because the adherent properties of a gum resin-based biological dressing allow for extended and continuous exposure of a skin lesion to drug, reduced concentration formulations are possible and even preferred. The amount to be used can therefore be adjusted as appropriate. Generally, the amount used will be within the range of ±25% of the indicated concentration, preferably within ±10% of the indicated concentrations. In the following paragraphs, the percentages appearing in parenthesis after the name of a particular agent represent the concentration(s) of agent that is(are) used in existing topical formulations.

The subject biological dressings find particular use in treating numerous dermatological disorders, including superficial infections (fungal, bacterial, viral and parasitic), and inflammatory skin disorders. Additional uses include sustained delivery of pharmacological agents for hair growth stimulation and hair growth retardation, skin pigmenting and pigmentation removal agents, sunscreens, insect repellents, anti-anginal, anti-perspirant and anti-nausea agents.

Superficial fungal infections treatable by the subject compositions include those caused by mold-like fungi (dermatophytes or tinea) or yeast-like fungi (*Candida*) that are confined to the stratum corneum or squamous mucosa. Particularly considered is the treatment of tinea infections including athlete's foot (tinea pedis), ringworm (tinea capitis), jock itch (tinea cruris), tinea corporis, tinea manuum and tinea versicolor. Other dermatological fungal infections treatable with the described biological dressings include *Candida, Epidermophyton, Microsporum, Trichophyton* and *Pityrosporum* infections. Compositions for the treatment of superficial fungal infections will include at least one anti-fungal pharmaceutical agent. Anti-fungal agents for use in a biological dressing composition include those well-known in the art, such as clotrimazole (0.5%, 1.0%, 2.0%), ketoconazole ((1%, 2%), econazole (1%), miconazole (2%), terconazole (0.4%), butoconazole (2%), oxiconazole (1%), sulconazole (1%), ciclopirox olamine (1%), haloprogin (1%), tolnaftate (1%), amphotericin B (3%), butenafine (1.0%), terbinafine (1.0%), naftifine, nystatin and griseofulvin. References that can be consulted to aid in the selection of an appropriate pharmacological agent include Goodman and Gilman's "The Pharmacological Basis of Therapeutics", $9^{th}$ Edition, 1996, Pergamon Press, New York, and the lastest edition of the Physician's Desk Reference published by Medical Economics Company, Montvale, N.J.).

Secondary bacterial infections that may arise in conjunction with the primary fungal infection can be treated simultaneously or prophylactically by additionally including a topically compatible antibiotic pharmacological agent in the biological dressing. Antibiotic medications known in the art that will find use in preparation of the subject compositions include clindamycin (1%), erythromycin (1.5%, 2.0%), tetracycline (3%), mupirocin (2.0%), gentamycin (0.1%), metronidizole (0.75%, 1%), bacitracin, neomycin and polymyxin B. A composition with a combination of antibiotics against different strains of bacteria will be preferred for certain treatments. A steroidal pharmacological agent, such as betamethasone (0.025%, 0.05%, 0.1%), in a biological dressing intended to treat a fungal infection can additionally be included to enhance the retraction of the lesion.

Biological dressings having an antibiotic medication as the primary pharmacological agent can be prepared to treat other skin disorders for which such medications are traditionally used, including as impetigo contagiosa, acne vulgaris, other superficial skin infections of unknown etiology, and post-operative superficial skin infections (e.g., infections that occur around the insertion of a catheter). Wound healing can be aided and colonization of wounds (i.e. isolated areas with first-degree burns) can be inhibited by application of a biological dressing comprising silver sulfadiazine (1%). The particular antibiotic selected to include in the biologic dressing will of course depend on the agents to which the strain of bacteria causing the infection is sensitive, and the specific needs of the patient.

A gum resin dressing can also be prepared for the treatment of superficial parasitic infections, such as scabies, nits and lice (including head lice and crab lice). For treating such infections, pharmacological compositions comprising miticides or pediculocides such as crotamiton (10%) or permethrin (5%), lindane (1%), malathion (0.003%, 0.06%, 0.5%), benzyl benzoate (26% to 30%), thiabendazole and pyrethrins.

For treating pain associated with arthritis, joint inflammation and muscle pain a gum resin dressing can be prepared containing one or more active ingredients such as menthol (10%), methyl salicylate (10%) and capsaicin (0.01%–10%) or a corticosteriod (see below for appropriate compounds and dosages). The biological dressing compositions also find use in the treatment of dermatological inflammatory disorders, wherein the primary pharmacological agent included is a corticosteroid. Particularly contemplated is the treatment of corticosteroid-responsive inflammatory conditions, such as atopic dermatitis or eczema, seborrheic dermatitis, some forms of psoriasis, apthous ulcers (canker sores), superficial skin lesions due to contact with poisonous plants such as poison oak or poison ivy, insect bites, and other skin rashes of unknown etiology. Steroidal agents of all different grades (1–7) that are known in the art can be included in a biological dressing preparation, such as betamethasone (0.025%, 0.05%, 0.1%), clobetasol (0.05%), diflorasone (0.05%), amcinonide (0.1%), desoximetasone (0.05%, 0.25%), fluocinonide (0.05%), halsinonide (0.1%), triamcinolone (0.025%, 0.1%, 0.5%), hydrocortisone (0.1%, 0.2%, 0.5%, 1.0%, 2.5%), flurandrenolide (0.05%), alclometasone (0.05%), fluocinolone (0.01%, 0.025%, 0.2%), desonide (0.05%), desamethasone (0.1%) and methylprednisolone (1.0%), clocortolone (0.1%), fluticasone (0.05%, 0.005%), mometasone (0.1%), prednicarbate (0.1%), amcinonide (0.1%), and halobetasole (0.05%). The particular corticosteriodal agent selected will depend on the patient and the dermatological disorder being treated.

For the treatment of certain skin disorders, non-steroidal drugs may be appropriate. As an example, a biological dressing comprising salicylic acid (2.5%, 5%, 10%, 20%, 40%, 60%) would be suitable for the treatment of acne, psoriasis, warts, and other hyperkeratotoic disorders. Cantharidin (0.7%), imiquimod (5%), and podofilox (0.5%) are other examples of pharmacological agents for use in a biological dressing prepared for the treatment of warts, including genital warts. Other pharmacological agents suitable for the treatment of acne include tretinoin (0.025%, 0.05%, 0.1%, 0.2%), isotretinoin, adapaline (0.1%), azelaic acid (20%), clindamycin, erythromycin, tetracycline, benzoyl peroxide (2.5%, 5%, 10%), and sulfacetamide (10%). A gum resin composition comprising metronidazole (0.75%) finds use in the treatment of rosacea. Biological dressings comprising anthralin (0.1%, 0.2%, 0.25%, 0.4% and 0.5%), calcipotriene (0.005%) and/or tazarotene find use in the treatment of psoriasis.

For certain inflammatory dermatological conditions, it may be desirable to include one or more anti-histamine compounds with a steroidal compound in the biological dressing compositions to aid in relieving itching that is often associated with inflammatory lesions. Histamine $H_1$ and $H_2$ receptor blockers known in the art are of use in the preparation of biologic dressings for treating certain inflammatory skin conditions include the $H_1$ blockers astemizole and terfenadine and the $H_2$ blocker cimetidine.

Dermatological conditions which can be treated with phamacological composition in which an anti-histamine is the primary agent include urticaria, and itching associated with lymphoproliferative diseases such as polycythemia rubra vera and Hodgkin's disease. Oftentimes best results are achieved when using both an $H_1$ and an $H_2$ blocker. Additionally, a medicated gum resin dressing comprising the anti-pruritic doxepin (5%) finds use in relieving the itching in patients with certain types of eczema. Topical doxepin appears to work by preventing the effects of histamine.

A gum resin carrier also finds use in the treatment of superficial dematological viral infections, whenever topical anti-viral medications would be indicated. Particularly considered is the administration of acyclovir (5%) for the treatment of viral infections caused by herpes (type 1 and type 2) simplex viruses, but a biological dressing can also be applied to superficial skin infections caused by papillomavirus (for example, common and genital warts). Other examples of anti-viral agents for use in a biological dressing include gancyclovir, penciclovir (1%), vidarabine (3%), idoxuridine (0.5%) and trifluridine.

A biological dressing also finds use in providing relief from pain associated with the lesions caused by some dermatological disorders. Particularly considered is treatment of the dermal pain that can be associated with varicella-zoster virus (shingles, chicken pox) with a topically compatible local anesthetic. A preferred pharmacological agent for use in a gum resin-based dressing prepared for treating pain associated with dermatological disorders is lidocaine (0.5%, 1%, 2%, 5%, 10%, 20%, 25%, see U.S. Pat. Nos. 5,709,869, 5,601,838, 5,589,180 and 5,411,738). Other local anesthetics chemically and/or pharmacologically related to lidocaine, or lidocaine hydrochloride, include bupivacaine hydrochloride (0.25%, 0.5%, 0.75%, 1.5%), etidocaine hydrochloride (1.0%, 1.5%, 3.0%), mepivacaine hydrochloride (1.0%, 1.5%, 2.0%, 3.0%, 5.0%), prilocaine hydrochloride (4.0%, 8.0%), and tetracaine hydrochloride (0.5%, 1.0%, 2.0%). Other preferred local anesthetics are those with low solubility in water, and which are particularly suited for sustained local anesthetic action when topically applied. Examples of local anesthetics with low solubility in water include benzocaine and the hydroiodide salt of tetracaine. Additional local anesthetics used in treating mucous membranes and the skin include dibucaine, dyclonine hydrochloride (0.5%, 1.0%), and pramoxine hydrochloride (1.0%), Another example of a pharmacological agent used topically to relieve dermatological pain includes capsaicin (0.025%).

Gum resin compositions containing synthetic hormones find use in the treatment of indications associated with abnormal hormone production as well as contraception. For example, a gum resin composition containing transdermal testosterone, generally about 2.5–5.0 mg per application, or equivalent other androgenic compound(s) in an appropriate amount can be used to treat young males with congenital or acquired primary hypogonadism, or congenital or acquired hypogonadotropic hypogonadism and other similar disorders. In women, a gum resin composition containing estradiol (an active form of estrogen) or other equivalent estrogenic compound(s) in an appriopriate amount, can be used to treat the indications and symptoms associated with atrophic vaginitis, atrophic dystrophy of the vulva, menopausal symptoms, female hypogonadism, ovariectomy, primary ovarian failure, non-steroid dependent inoperable breast cancer and vasomotor symptoms associated with menopause and prevention of post-menopasual osteoporosis. A gum resin composition containing an estrogenic compound, such as for example estradiol in an amount sufficient for the treatment of such indications is used.

A composition containing norethindrone (progestin) can be used to prevent pregnancy by inhibiting ovulation and thickening the mucosa of the cervix. In addition, a gum resin composition containing a progestin compound such as norethindrone (0.14–0.25 mg per application) can be used for treating abnormal menstrual disorders such as amenorrhea, abnormal uterine bleeding and endometriosis, applications generally will be to the skin. The site of application of the gum resin composition will vary depending upon the intended use. Generally the site of application will be to the skin at a location that will provide for absorption into the blood stream. Particularly in the case of treatments relating to the female genitalia, application can be intravaginally Gum resin compositions are also suitable for sustained delivery of pharmacological agents use for hair growth retardation and stimulation. For treatments intending to stimulate hair growth, compositions comprising minoxidil (1%, 2%, 5%) are prepared. For other topical formulations that can be used with the gum resins, see U.S. Pat. No. 6,184,249. For treatment intending to retard hair growth compositions comprising eflornithine hydrochloride (13.9%) are prepared.

A gum resin vehicle additionally finds use in preparing protective compositions comprising sun protecting, ultraviolet absorptive agents. Sunscreens for use in a gum resin-based dressing include aminobenzoate agents, such as p-aminobenzoic acid (PABA), ethyl 4-[bis(hydroxypropyl)] aminobenzoate, octyl dimethyl PABA, PABA propoxylate, glyceral PABA, 2-ethylhexyl PABA and pentyl PABA; cinnamate agents, such as cinoxate, diethanolamine-p-methoxy cinnamate, 2-ethylhexyl-p-methoxycinnamate and octyl methoxycinnamate; benzones, such as oxybenzone, dioxybenzone, sulisobenzone; salicylates, such as 2-ethylhexyl salicylate, triethanol amine salicylate, and octyl salicylate; and other sunscreen agents, such as titanium dioxide and zinc oxide. For use as a sunscreen, generally a thin gum resin/ultraviolet absorptive agent preparation is applied to areas of the skin that will be exposed to the sun. For some situations, protection of exposed skin from the sun will be best accomplished by applying a thicker gum resin formulation, for example, for application of sunscreen to protect the skin of the nose at high altitudes.

Advantageously, a gum resin/sunscreen compound formulation is particularly effective at providing long-lasting sun protection to exposed skin through resisting removal by abrasion or moisture Gum resin compositions may be prepared with pharmacological agents used for pigmenting or de-pigmenting the skin, for instance, for use in treating patients with vitiligo. For treatments intending to de-pigment or lighten isolated dermal areas, a pharmacologic composition comprising hydroquinone (2%, 3%, 4%) is prepared. For treatments intending to pigment desired areas of skin, a composition comprising a psoralen agent, such as methoxalen (1.0%), for combined use with UV light, is prepared.

A medicated dressing will also find use in the sustained delivery of anti-perspirants, anti-anginal, anti-nausea agents and anti-cancer agents. Particularly contemplated are compositions comprising aluminum chloride (20%), for the inhibition of perspiration of isolated dermal areas, for instance to aid in carrying out surgical procedures. A gum resin composition comprising nitroglycerin (0.5%, 1.0%, 2.0%) will find use in the sustained transdermal delivery of this anti-anginal agent which can provide relief from chest pains. Relief from nausea, due to motion sickness for example, can be provided using a biological dressing comprising scopolamine. For anti-nausea purposes, a gum resin/scopolamine composition would be applied, behind the ear for example, before the onset of activity that potentially would induce nausea. Additionally, a gum resin dressing can be prepared for the sustained delivery of pharmacological agents useful in the treatment of superficial cancerous and pre-cancerous lesions. Particularly contemplated is the treatment of isolated actinic keratosis lesions with a biological dressing comprising 5-fluorouracil (5-FU; 5%, 10%).

A gum resin carrier may also be prepared with an insect repellant as the pharmacologic agent. Examples of insect repellant compounds suitable for inclusion in a biological dressing include terpenoids, such as citronellal, geraniol, terpentine, pennyroyal, cedarwood, eucalyptus and wintergreen; benzoquinones; aromatics, such as cresols, benzaldehyde, cinnamic aldehyde, benzoic acids; and synthetic insect repelling agents, such as N,N-diethyl-m-toluamide (DEET), ethyl hexanediol, dimethyl phthalate, dimethyl ethyl hexanediol, carbate, butopyronoxyl, di-n-propyl isocinchonmeronate, N-octyl bicycloheptene, dicarboximide, and 2,3,4,5-bis(2-butylene) tetra-hydro-2-furaldehyde. For use as an insect repellent, a gum resin preparation is preferably applied as a thin coat to areas of the skin most likely to be attacked by an insect. Preferably, the insect repellant compound used repels insects without irritating the skin. Advantageously, as with the sunscreen preparations described above, a gum resin/insect repellent formulation is particularly effective at providing long-lasting insect repellency on the skin through resisting removal by abrasion or moisture.

Gum resin compositions also find use in the treatment of drug addiction. Compositions containing nicotine, generally about in an amount sufficient to decrease nicotine addition, 14–22 mg per application, or other amounts as appropriate, find use in the reduction and/or cessation of cigarette smoking, chewing tobacco or other nicotine containing compounds. The compositions are applied to the skin in a location that provides sufficient absorption of the nicotine, typically the upper arm. As the need for nicotine decreases the dosage of nicotine in the composition can be adjusted downward.

Optionally, the biologic dressing may include a penetration enhancer, i.e., a chemical compound that, when included in a formulation, temporarily increases the permeability of the skin to a drug allowing more of the drug to be absorbed in a shorter period of time. Examples of penetration enhancers that can be used include dimethylsulfoxide, n-decyl methyl sulfoxide, N,N-dimethylacetamide, N,N-methyl-2-pyrrolidone and octylphenylpolyethylene glycols.

The biologic dressing may also include other pharmaceutically acceptable carriers as needed that do not adversely affect the effectiveness of the drug, or the resinous delivery vehicle and do not damage the skin to which it is applied. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethyl-cellulose; sodium alginate; poly(vinyl pyrrolidone); and the like, alone, or with suitable dispensing agents such as lecithin; polyoxyethylene stearate; and the like. The carrier may also contain adjuvants such as preserving stabilizing, wetting, emulsifying agents and the like.

In practicing a method of treating the symptoms of a dermatological disease in a patient, the pharmacological composition in its original prepared form, is applied directly and specifically on the lesions or other damaged areas of skin requiring treatment. The biological dressing composition may initially be prepared in any form suitable for topical application, such as a paste, a liquid, a semi-solid, a gel, a suspension, an emulsion or the like, provided that the formulation allows the gum resin carrier and pharmacologically active agent to effectively adhere together to the skin surface to which they are applied and to form a protective barrier over the skin once the volatile solvent has evaporated. To minimize waste, application is generally carried out by painting or swabbing the composition at the affected site or sites, but certain preparations can also be applied by spraying on the formulation, and allowing it to dry. The biologic dressing composition can be applied wherever the patient has superficial skin lesions or infections, such as on cutaneous areas, mucous membranes, and mucocutaneous junctions (i.e., perianal, intertriginous and vulvovaginal areas). After application, the volatile solvent evaporates to leave a protective solidified, adherent and hydrophobic film or coating on the skin surface to which it has been applied. The solidified film residue comprises the gum resin carrier, and the pharmacologically active agent or agents. By forming a barrier holding the pharmacologically active agent to the surface, the gum resin permits a sustained, continuous release and a prolonged exposure to the agent or agents. Continuous exposure of the skin to the medication is maintained as long as the coating stays in place. The biologic dressing, therefore can effect symptomatic relief with less frequent applications. For most dermatological disorders treated using a gum resin-based dressing, one or two daily applications will be sufficient to promote regression or disappearance of the targeted skin lesions. For certain less respondent lesions, three daily applications may be required to effect disappearance of symptoms. Other dermatological disorders may require application every second day to realize symptomatic relief. The composition conveniently can be removed at will, by application of an appropriate solvent, normally ethanol. The composition can also be removed by scrubbing with soap and water.

The invention now being generally described, it will be more readily understood by reference to the following examples which are included for purposes of illustration only and are not intended to limit the present invention.

EXAMPLES

Example 1

Treatment of Athlete's Foot (Tinea Pedis) with a Gum Resin-based Biological Dressing Comprised of Tinture of Benzoin and Clotrimazole Tincture of benzoin compositions are produced with standard tincture of benzoin (3M, Minneapolis, Minn.). Replicated experiments were performed with a composition comprising tincture of benzoin with 60% alcohol plus 1% clotrimazole. To determine efficacy in treating athlete's foot, the benzoin/clotrimazole composition was applied to cases of athlete's foot, replicated 5 times. In each replicate, the composition led to complete clearance of the athlete's foot within 1 week, when applied twice daily for 7 days. No allergic reaction was noted in this test, although the alcohol component reportedly led to stinging when applied to deep fissures. Minimal lint from the socks was noted on the coating where the composition was applied but was easily removed with ethanol. Efficacy of the benzoin/clotrimazole composition was compared to controls of tincture of benzoin alone and no treatment. The benzoin/clotrimazole composition provided symptomatic relief and led to healing more quickly than tincture of benzoin alone, though tincture of benzoin alone improved symptoms and signs more quickly when compared to no treatment. This is likely due to the fact that the sticky coating from the tincture tends to repel moisture. Efficacy of the benzoin/clotrimazole composition also was compared to commercially available medications such as Lamisil®, Lotrimin®, Mycelex® and Tinactin®. In comparison, the benzoin/clotrimazole composition greatly decreased the time necessary for treatment compared to formulations of each of the commercial medications, particularly when the commercial medications were administered in the form of powder, liquid, solution, spray or gel. The benzoin/clotrimazole composition also decreased the time necessary for treatment when compared to cream versions of the above medications and was much less messy than any of the commercial preparations tested.

The above results demonstrate the improved symptomatic relief from a dermatological disorder that can be achieved by administering a topically acceptable pharmacological agent in a gum resin carrier that forms a biological bandage in comparison presently available carriers. With a gum-resin-based biological dressing, relief from the unpleasant symptoms associated with a dermatological lesion is realized more efficiently and in a more convenient and palatable manner.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

What is claimed is:

1. A pharmacological composition comprising: a) a gum resin, wherein said gum resin comprises benzoin; b) at least one topically acceptable pharmacologically active agent other than said gum resin that is effective as a treatment for ameliorating symptoms of a disease of skin or a mucous membrane of a mammal, wherein said pharmacologically active agent can remain in contact with said skin or said mucous membrane greater than 6 hours without toxic effects to said mammal; and c) a topically acceptable volatile solvent for said gum resin and said pharmacologically active agent.

2. The composition according to claim 1, wherein said topically acceptable volatile solvent comprises ethanol.

3. The composition according to claim 2, wherein said topically acceptable volatile solvent is ethanol and comprises about 60% to 90% of said composition.

4. The composition according to claim 1 wherein said pharmacologically active agent is an antimicrobial agent.

5. The composition according to claim 4, wherein said antimicrobial agent is an anti-fungal agent.

6. The composition according to claim 5, wherein said anti-fungal agent is clotrimazole.

7. The composition according to claim 6, wherein said clotrimazole is present as 1% of said composition.

8. The composition according to claim 1 wherein said pharmacologically active agent is a steroidal agent.

9. The composition according to claim 8, wherein said steroidal agent is betamethasone.

10. The composition according to claim 9, wherein said betamethasone is present as 0.025–0.05% of the composition.

11. The composition according to claim 1, wherein said pharmacologically active agent comprises both an antimicrobial agent and a steroidal agent.

12. The composition according to claim 1, further comprising a penetration enhancer.

13. A pharmacological composition comprising: a) a benzoin; b) clotrimazole; and c) ethanol.

14. A pharmacological composition comprising: a) a benzoin; b) 1% clotrimazole; and c) 60% ethanol.

15. The composition according to claim 4, wherein said antimicrobial agent is an anti-viral agent.

16. The composition according to claim 4, wherein said antimicrobial agent is an anti-bacterial agent.

17. The composition according to claim 16 wherein said antibacterial agent is an antibiotic.

18. The composition according to claim 1 wherein said pharmacological agent is a hormone.

19. The composition according to claim 1 wherein said pharmacological agent is an anti-histamine.

20. The composition according to claim 5, wherein said anti-fungal agent is terbinafine.

21. The composition according to claim 19, wherein said terbinafine is present as 1% of said composition.

22. A pharmacological composition comprising: a) a benzoin; b) terbinafine; and c) ethanol.

23. A pharmacological composition comprising: a) a benzoin; b) 1% terbinafine; and c) 60% ethanol.

24. A pharmacological composition comprising: a) a benzoin; b) ciclopirox olamine; and c) ethanol.

25. A pharmacological composition comprising: a) a benzoin b) 1% ciclopirox olamine; and c) 60% ethanol.

* * * * *